United States Patent [19]

Handrick et al.

[11] 4,384,152

[45] May 17, 1983

[54] ANTHRACENE PRODUCTION FROM PHENANTHRENE

[75] Inventors: Kurt Handrick, Essen-Steele; Georg Kölling, Essen; Fritz Mensch, Essen-Steele, all of Fed. Rep. of Germany

[73] Assignee: Bergwerksverband GmbH, Essen, Fed. Rep. of Germany

[21] Appl. No.: 218,000

[22] Filed: Dec. 18, 1980

[30] Foreign Application Priority Data

Dec. 22, 1979 [DE] Fed. Rep. of Germany ....... 2952062

[51] Int. Cl.$^3$ .......................... C07C 1/00; C07C 2/00; C07C 4/00
[52] U.S. Cl. .................................... 585/320
[58] Field of Search ........................ 585/320

[56] References Cited

U.S. PATENT DOCUMENTS 3,389,188  6/1968  Michalowicz ................. 585/320 X

FOREIGN PATENT DOCUMENTS 694961  7/1953  United Kingdom ................ 585/320

OTHER PUBLICATIONS

Olah, "Friedel–Crafts and Related Reactions," vol. 1, pp. 298–299 (1963).

*Primary Examiner*—Robert V. Hines
*Attorney, Agent, or Firm*—Michael J. Striker

[57] ABSTRACT

A method for production of anthracene from phenanthrene is disclosed. Phenanthrene is hydrogenated at a nickel on a carrier catalyst at temperatures from about 140° C. to 170° C. under a pressure of from about 10 to 30 bar by gradual addition of hydrogen. The hydrogenation product is separated by distillation into sym.-octahydrophenanthrene and asym.-octahydrophenanthrene. The sym.-octahydrophenanthrene is isomerized in the presence of methylene chloride as a solvent and of aluminum chloride as a catalyst at a temperature from about −30° to +5° C. to sym.-octahydroanthracene. The sym.-octahydroanthracene is dehydrogenated at a chromium oxide-aluminum oxide catalyst at temperatures from about 450° to 550° C. to anthracene.

The resulting anthracene is obtained with high yield and is very pure after a single recrystallization step.

27 Claims, 1 Drawing Figure

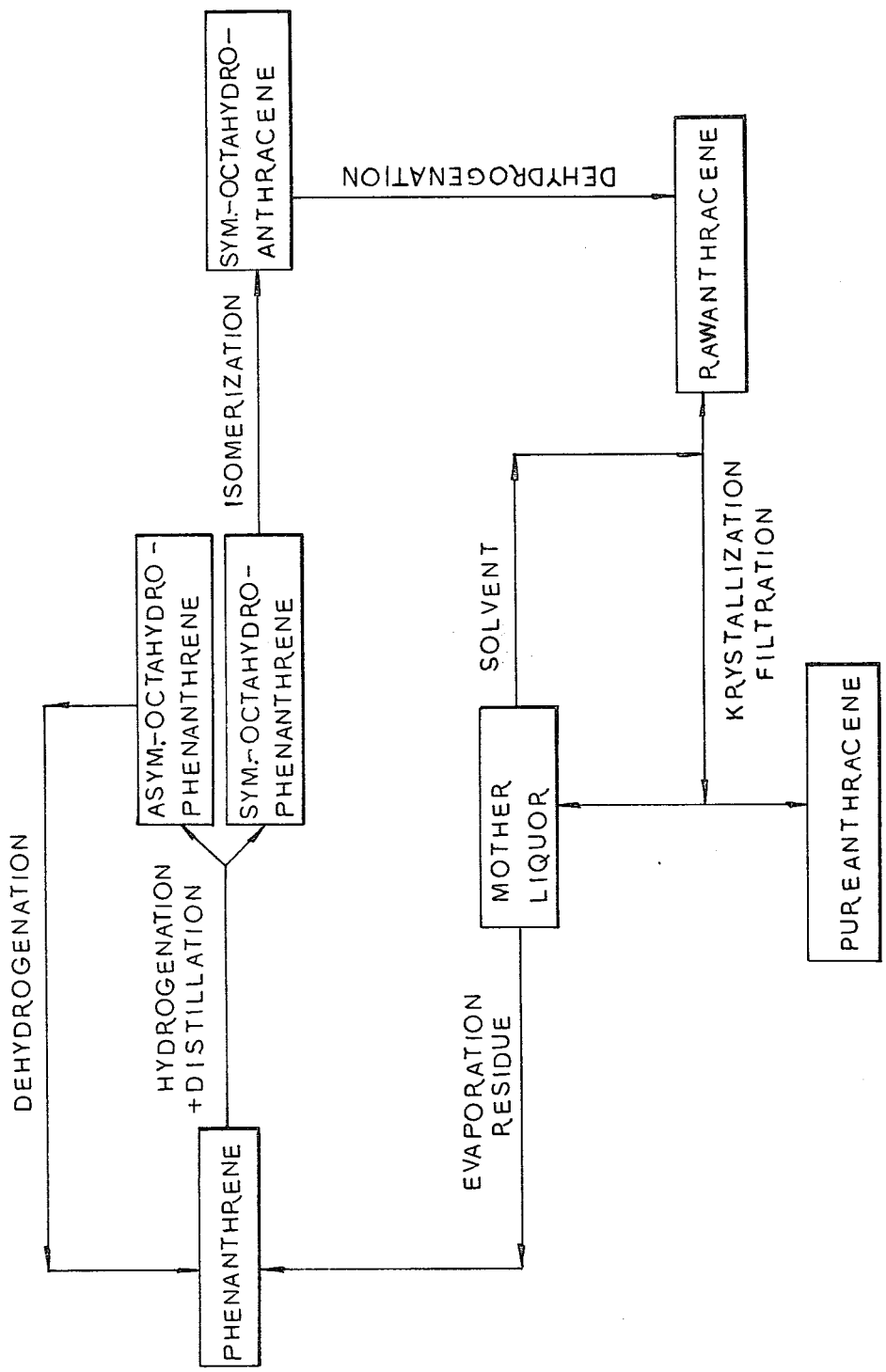

ANTHRACENE PRODUCTION FROM PHENANTHRENE

BACKGROUND OF THE INVENTION

1. Field of the Invention

The present invention relates to a method for producing anthracene from phenanthrene and to methods providing improved yields of intermediate products.

2. Brief Description of the Background of the Invention Including Prior Art

Phenanthrene and anthracene are generally obtained from bituminous coal tar containing about five weight percent of phenanthrene and from about 1.2 to 1.4 weight percent of anthracene. However, anthracene is the more valuable product since it serves in increasing amount in the production of anthraquinone coloring agents. Therefor, there has been no lack in attempts to transform phenanthrene into anthracene. The long known process of hydrogenating phenanthrene to sym.-octahydrophenanthrene, isomerizing the sym.-octahydrophenanthrene to sym.-octahydroanthracene and dehydrogenating the sym.-octahydroanthracene to anthracene has been subject of a number of proposals trying to improve the yield and to simplify technically the reaction steps.

It is already known to perform the hydrogenation of phenanthrene such as to yield to a large extent sym.-octahydrophenanthrene [Journal of the American Chemical Society 59 (1937) 135 and 60 (1938) 1501–1505]. It is disclosed that in the presence of a nickel on a carrier catalyst about 9 percent asym.-octahydrophenanthrene and about 91 percent sym.-octahydrophenanthrene are obtained from phenanthrene dissolved in diethylcyclohexane at a temperature of 191° C. to 198° C. and under a hydrogen pressure of 56 bar after 3.5 hours and the sym.-octahydroanthracene is separated from the reaction mixture by distillation [German Offenlegungsschrift DE-OS No. 16 18 597]. The easy formation of undesired perhydrophenanthrene (tetradecahydrophenanthrene) is in fact suppressed by the employment of a solvent, however the cost of the process is increased.

It is also known to isomerize sym.-octahydrophenanthrene to sym.-octahydroanthracene in the presence of aluminum chloride at 70° C. to 80° C. The resulting mixture contains about 12 percent of higher condensed by-products and the remaining 88 percent contain to about half in each case of the two isomers [Berichte 57 (1924) 1990–2024]. It is furthermore known to perform the isomerisation with 2.5 to 5 weight percent aluminum chloride based on the sym.-octahydrophenanthrene at a temperature of 5° to 45° C. and preferably 20° to 35° C. during a reaction time of from about 10 to 24 hours.

Following, the product is taken up with toluene and is processed as usual. About 93 to 96 weight percent of the starting material amount are recovered, which are composed as follows:

87–90 weight percent mixture of the isomers of sym.-octahydroanthracene and sym.-octahydrophenanthrene as well as 10–13 weight percent of higher condensed by-products. The contents of the isomer mixture in sym.-octahydroanthracene amounts to 81–96 weight percent [German patent disclosure DE-AS 857 042].

In view of the whole process, the isomerization of the sym.-octahydrophenathrene is of particular importance, since a high degree of isomerization and a low formation of by-products are decisive for the success of the process.

SUMMARY OF THE INVENTION

1. Purposes of the Invention

It is an object of the invention to improve the isomerization of sym.-octahydrophenanthrene to sym.-octahydroanthracene.

It is another object of the invention to improve the hydrogenation of phenanthrene to sym.-octahydrophenanthrene.

It is a further object of the invention to improve the dehydrogenation of sym.-octahydroanthracene to anthracene.

It is an additional object of the invention to fully use by-products such as asym.-octahydrophenanthrene and as the residues resulting in the purification of the product to anthracene.

It is an overall object of the present invention to improve the production of anthracene from phenanthrene and to obtain a purer anthracene more easily.

These and other objects and advantages of the present invention will become evident from the description which follows.

2. Brief Description of the Invention

The present invention provides improvements in the production of anthracene from phenanthrene.

In one aspect of the invention there is improved the production of anthracene by hydrogenation of phenanthrene in the presence of a nickel catalyst at elevated temperature and pressure for forming sym.-octahydrophenanthrene, by isomerization of the same in the presence of an aluminum chloride catalyst at lower temperature to sym.-octahydroanthracene and by catalytic dehydrogenation of the sym.-octahydroanthracene in several ways. The phenanthrene is hydrogenated at a nickel catalyst on a support at a temperature of from about 140° C. to 170° C. and preferably from about 150° C. to 160° C. and under a pressure from about 10 to 30 bar by gradual addition of hydrogen.

The hydrogenation product is separated by distillation into sym.-octahydrophenanthrene and asym.-octahydrophenanthrene. The sym.-octahydrophenanthrene is isomerized in the presence of methylene chloride, preferably in an amount of 15 to 60 weight percent and more preferably in an amount from about 25 to 50 weight percent based on the amount of sym.-octahydrophenanthrene employed, as a solvent and of aluminum chloride, preferably in an amount of from about 3 to 6 percent and more preferred in an amount of from about 4 to 5 weight percent based on the amount of sym.-octahydrophenanthrene employed, as a catalyst at a temperature from about $-30°$ C. to $+5°$ C. and preferably from about $-10°$ to $0°$ C. to sym.-octahydroanthracene. The sym.-octahydroanthracene is dehydrogenated at a chromium oxide-aluminum oxide catalyst at a temperature from about 450° C. to 550° C. and preferably at a temperature from about 480° C. to 520° C.

The asym.-octahydrophenanthrene resulting from the separating by distillation can be dehydrogenated at a chromium oxide - aluminum oxide catalyst to phenanthrene and the phenanthrene can be fed back as phenanthrene to be hydrogenated.

The product of the dehydrogenation can be recrystallized from a solvent to obtain pure anthracene. The mother liquor resulting from the recrystallization followed by evaporation of the solvent can be employed as a starting material in the hydrogenation process.

In a further aspect of the invention there is provided a method for hydrogenation of phenanthrene to sym.-octahydrophenanthrene which comprises contacting phenanthrene with hydrogen at pressures from about 10 to 40 bar and at temperatures from about 140° C. to 170° C. and preferably from about 150° C. to 160° C. in the presence of a nickel catalyst for a time sufficient to effect hydrogenation. The nickel acting catalytically can be deposited on a carrier and the amount of catalyst can be from 0.1 to 1.0 weight percent. A preferred pressure range is from about 20 to 30 bar.

In a further aspect of the invention a method is provided for isomerizing sym.-octahydrophenanthrene to octahydroanthracene which comprises contacting the sym.-octahydrophenanthrene with an acid catalyst, preferably aluminum chloride, in a preferred amount of from about 3 to 6 weight percent and more preferred amount of 4 to 5 weight percent based on the amount of the sym.-octahydrophenanthrene, in the presence of a solvent, preferably a halohydrocarbon having a melting point below −30° C. and a boiling point above −10° C., at a temperature suitable for crystallization of sym.-octahydroanthracene for a time sufficient to effect isomerization. The halohydrocarbon preferably contains at least one chlorine atom for each carbon atom in the molecule and a preferred halohydrocarbon is methylene chloride. The amount of halohydrocarbon employed is preferably from about 15 to 60 weight percent and more preferred from about 25 to 50 weight percent based on the amount of sym.-octahydrophenanthrene employed. The contacting temperature is preferably from −30° to +5° C. and more preferred is a contacting temperature from about −10° C. to 0° C.

There is also provided a method for dehydrogenation of sym.-octahydroanthracene to anthracene which comprises contacting the sym.-octahydroanthracene with a chromium oxide - aluminum oxide catalyst at a temperature of from about 450° C. to 550° C. and preferably from about 480° C. to 520° C. for a time sufficient to effect dehydrogenation. The contacting is preferably performed in the presence of a carrier gas.

The invention accordingly consists in the series of steps which will be exemplified in the method hereinafter described and of which the scope of application will be indicated in the appended claims.

BRIEF DESCRIPTION OF THE DRAWING

In the accompanying drawing is shown one of the various possible embodiments of the invention:

FIG. 1 is a view of a schematic diagram showing the steps in a preferred embodiment of transforming phenanthrene into anthracene.

DESCRIPTION OF INVENTION AND PREFERRED EMBODIMENTS

In accordance with the present invention a process is disclosed for producing anthracene by hydrogenation of phenanthrene in the presence of a nickel catalyst at elevated temperature and elevated pressure under formation of sym.-octahydrophenanthrene, isomerizing of the same in the presence of an aluminum chloride catalyst at lower temperature to sym.-octahydroanthracene and catalytic dehydrogenation of the sym.-octahydroanthracene. The phenanthrene is hydrogenated at a catalyst comprising nickel on a carrier at a temperature from about 140° to 170° C. and preferably from about 150° C. to 160° C. under a pressure from about 10 to 30 bar with gradual addition of hydrogen. The hydrogenation product is separated by distillation into sym.-octahydrophenanthrene and asym.-octahydrophenanthrene. The sym.-octahydrophenanthrene is isomerized to sym.-octahydroanthracene in the presence of a solvent and of a catalyst, preferably methylene chloride and aluminum chloride, at a temperature from about −30° C. to +5° C. and preferably from about −10° C. to 0° C. The sym.-octahydroanthracene is dehydrogenated at a chromium oxide aluminum oxide catalyst at a temperature from about 450° C. to 550° C. and preferably from about 480° C. to 520° C.

In a preferred embodiment of the invention the asym.-octahydrophenanthrene separated in the distillation is dehydrogenated at a chromium oxide - aluminum oxide catalyst to phenanthrene and this is fed back to the hydrogenation step.

In particular in accordance with the present invention an increased yield can be obtained by isomerizing the sym.-octahydrophenanthrene in the presence of about 3 to 6 weight percent and preferably 4 to 5 weight percent aluminum chloride and of about 15 to 60 weight percent and preferably from 25 to 50 weight percent of methylenechloride, the weight percentages referring to the amount of sym.-octahydrophenathrene employed. Also, for the same purpose, in accordance with the present invention the evaporation residue of the mother liquor generated in the recrystallization of the raw anthracene is fed back to the hydrogenation stage.

In accordance with the invention, the phenanthrene is hydrogenated to sym.-octahydrophenanthrene in fact at a nickel catalyst, however at a lower temperature and at a lower pressures and without the addition of a solvent. In particular, the hydrogenation is performed in the absence of diethylcyclohexane. These steps including the absence of a solvent avoid overhydrogenation of the phenanthrene. 0.1 to 1 weight percent of catalyst are completely sufficient. The hydrogenation starts at about 140° C. and can be continued at from about 150° C. to 160° C. It is necessary, especially at the beginning, to keep the amount of hydrogen available low in order to assure a moderate reaction of the exothermic process. This can be achieved for example by adjusting the hydrogen pressure to 10 to 40 bar and preferably to 20 bar. After about 5 hours the hydrogenation is terminated. A mixture is obtained containing in addition to about 95 weight percent sym.-octahydrophenanthrene also about 5 weight percent asym.-octahydrophenanthrene. It is separated in a distilling column with a good separation effect.

The separated asym.-octahydrophenanthrene can be dehydrogenated at about 500° C. over a chromium oxide - aluminum oxide catalyst disposed in a fixed bed and the phenanthrene formed can be anew subjected to hydrogenation. This way there are practically no losses in material occuring during the hydrogenation step.

The isomerization of sym.-octahydrophenanthrene to sym.-octahydroanthracene is performed in the presence of an acid catalyst and of a solvent. The preferred acid catalyst is aluminum chloride. Preferred solvents include halohydrocarbons containing fluorine, chlorine and/or bromine and having melting points below −30° C. and boiling points above −10° C. Preferred halohydrocarbons have at least one chlorine atom for each carbon atom and preferably two chlorine atoms for each carbon atom. Such halohydrocarbons include chloroform, dichloromonofluoromethane, fluorobromomethane, 1,1,1-trichlorodifluoroethane, methylenechloride and mixtures thereof. Preferably, methylenechloride is employed. Preferably, sym.-octahydrophenanthrene is isomerized to sym.-octahydroanthracene in the presence of from about 3 to 6 weight percent and preferably of from about 4 to 5 weight percent of aluminum chloride, based on the weight of the material to be isomerized, at temperatures from about −30° to +5° C. and preferably from about −10° to 0° C. in the presence of from about 15 to 60 weight percent and preferably of 25 to 50 weight percent of methylenechloride as a solvent, again referring to the weight of material to be isomerized. The solvent effects a crystalline deposition of the sym.-octahydroanthracene at the relatively low temperatures and thereby removes the same from the isomerization equilibrium. There is always a liquid phase present wherein the reaction can continue to run. In any case the mixture should remain capable of being stirred even at the end of the reaction. When in accordance with the present invention methylene chloride is employed as the solvent, then a soluble complex is formed from the methylenechloride with the aluminum chloride and the sym.-octahydrophenanthrene such that the reaction runs in a homogeneous phase. After about 6 to 7 hours the reaction is completed. The reaction product contains only about 3 to 4 weight percent of higher condensed products, which remain in the residue in the following distillation. The isomer mixture separated by distillation contains about 96 to 97 weight percent sym.-octahydroanthracene and 3 to 4 weight percent sym.-octahydrophenanthrene. It can be subjected immediately to dehydrogenation without prior separation of the isomers.

Then the sym.-octahydroanthracene is dehydrogenated at a chromium oxide - aluminum oxide catalyst at temperatures from about 450° C. to 550° C. and preferably from about 480° C. to 520° C. and preferably with the addition of small amounts of an inert gas as a carrier gas such as for example also hydrogen. Advantageously, a preheat zone containing inert materials such as for example broken quartz pieces and running at a slightly lower temperature as the reaction zone is predisposed to the reaction zone proper.

The method according to the present invention results in the advantage of providing an anthracene of more than 99 percent purity after a single recrystallization of the raw product from a solvent such as for example pyridine, tetrahydronaphthalene or cyclohexanone. The evaporation residue from the mother liquor of the recrystallization containing substantially intermediate products of the dehydrogenation is fed back to the hydrogenation stage.

Considering all possibilities of recycling and feeding back in the individual stages the total yield amounts to about 92 to 93 percent of the theoretical value. In contrast in known procedures only yields of from 60 to 70 percent of the theoretical value are obtained.

The process of the present invention is illustrated in the schematic diagram of FIG. 1 and by way of the following examples.

In accordance with the schematic process diagram the phenanthrene is hydrogenated and the hydrogenation product is separated by distillation into asym.-octahydrophenanthrene and sym.-octahydrophenanthrene. The asym.-octahydrophenanthrene is fed back after dehydrogenation to the starting material. The sym.-octahydrophenanthrene is isomerized to the sym.-octahydroanthracene. This is then dehydrogenated to raw anthracene. The raw anthracene is recrystallized from a suitable solvent and pure anthracene is obtained. The mother liquor is heated to evaporate the solvent and the solvent is reused for further recrystallization procedures and the residue from the evaporation of the mother liquor is fed back to the starting material.

EXAMPLE 1

Hydrogenation of Phenanthrene (a) 2 g Harshaw nickel on a carrier catalyst (Ni-1404 P) were added to 1000 g desulfurized phenanthrene and placed in an autoclave with stirrer of about 2 liter capacity and the contents is heated under stirring to 150° C. after substitution of the air present by hydrogen. Then a hydrogen pressure of 20 bars is applied and the pressure maintained by continuous application of pressurized hydrogen. After about 5 hours during which the temperature had been increased to 160° C. a clear decrease in the acceptance of hydrogen is observed. Thus the hydrogenation is ended. After cooling of the contents of the autoclave the liquid reaction product is filtered off. The yield amounts to 1044 g. An analysis shows that the reaction product comprises 93.3 weight percent sym.-octahydrophenanthrene, 6.5 weight percent asym.-octahydrophenanthrene, 0.1 weight percent 9,10-dihydrophenanthrene and 0.1 weight percent of phenanthrene.

(b) 1000 g hydrogenation product were distilled in a 2 meter long distillation column with about 40 theoretical plates at a reflux ratio of 3:1 in a nitrogen atmosphere of a 12 torr vacuum. 59 g of asym.-octahydrophenanthrene (boiling point 153°–154° C. at 12 torr) were obtained and an additional 52 g of a transition fraction (boiling point 154° to 167° C. at 12 torr), which comprised substantially sym.-octahydrophenanthrene, and 710 g of sym.-octahydrophenanthrene (boiling point 167°–168° C. at 12 1 torr) of a purity of more than 99.5 percent.

The remaining parts in the bottom of the column of about 180 g were obtained when the next batch of the hydrogenation product, to which also the transition fraction was added, was subjected to distillation.

EXAMPLE 2

Dehydrogenation of asym.-octahydrophenanthrene 250 ml of broken quartz fragments, 500 ml $Cr_2O_3$/$Al_2O_3$ catalyst (Girdler 641-6×6 mm pellets) as well as another 250 ml of broken quartz fragments were filled from the bottom to the top into a vertical quartz tube located in an electrically heatable furnace. The preheat zone was heated to 450° C. and the following zones were heated to 500° C. 400 ml (402.5 g) asym.-octahydrophenanthrene per hour were added drop by drop from the upper end of the quartz tube. Through a side connection 4 liter hydrogen per hour were passed as a carrier gas. Then 385 g of a reaction product were obtained per hour, which consisted to 97.2 percent of phenanthrene. This was entered again at the hydrogenation stage.

EXAMPLE 3

Isomerization of sym.-octahydrophenanthrene 1000 g of the sym.-octahydrophenanthrene fraction of Example 1(b) and 250 ml methylene chloride were placed in a stirred flask and cooled to −10° C. Then 40 g of aluminum chloride powder were added in small quantities, while the temperature at times rose to −8° C. The mixture turning darkbrown was uniformly stirred. By crystallization of sym.-octahydroanthracene the addition of further 150 ml methylene chloride was required after about 4 hours. After an additional 2 hours 500 ml of 10 percent sodium hydroxide solution were added for decomposing the aluminum chloride, then the organic phase was separated and after removal of the solvent the organic phase was distilled in vacuum of 12 torr. There resulted in the sequence of the boiling points 5.5 g tetrahydronaphthalene (boiling point 82° C. at 12 torr), 958 g isomer mixture of a boiling point of 167°-168° C. at 12 torr comprising 97 percent sym.-octahydroanthracene and 3 percent sym.-octahydrophenanthrene, as well as a distillation residue of 34.8 g.

EXAMPLE 4

Dehydrogenation of sym.-octahydroanthracene

In the dehydrogenation apparatus described in Example 2 the preheating zone was heated to a temperature of 480° C. and the reaction and afterheat zone were heated to a temperature of 520° C. 400 ml molten sym.-octahydroanthracene (385 g) of Example 3 were added drop by drop per hour from a drip funnel heated to 95° C. At the same time about 4 liter hydrogen per hour were added as a carrier gas. 372 g of raw anthracene were obtained per hour, which contained as impurities 1.8 percent 9,10-dihydroanthracene, 2.5 percent 1,2,3,4-tetrahydroanthracene, 2.6 percent sym.-octahydroanthracene and 2.9 percent phenanthrene.

1000 g raw anthracene were dissolved under heating in 3.8 liters technical pyridine (base mixture) for purification. The crystals precipitating upon cooling of the solution were centrifuged, washed with little solvent and water and were dried. The yield of anthracene was 880 g with a purity of more than 99 percent (Melting point 216°-217° C.). The residue from evaporation of the mother liquor (about 118 g) was returned to the hydrogenation stage.

Without further analysis, the foregoing will so fully reveal the gist of the present invention that others can, by applying current knowledge, readily adapt it for various applications without omitting features that, from the standpoint of the prior art, fairly constitute essential characteristics of the generic or specific aspects of this invention.

What is claimed is:

1. A method for production of anthracene by hydrogenation of phenanthrene in the presence of a nickel catalyst at elevated temperature and elevated pressure by forming sym.-octahydrophenanthrene, by isomerization of the same in the presence of an aluminum chloride catalyst at lower temperature to sym.-octahydroanthracene and by catalytic dehydrogenation of the sym.-octahydroanthracene, the improvement comprising hydrogenating phenanthrene at a nickel catalyst on a support at a temperature from about 140° C. to 170° C. under a pressure of from about 10 to 30 bar by gradual addition of hydrogen;
separating the hydrogenation product by distillation into sym.-octahydrophenanthrene and asym.-octahydrophenanthrene;
isomerizing the sym.-octahydrophenanthrene in the presence of methylenechloride as a solvent and of aluminum chloride as a catalyst at a temperature of from about −30° C. to +5° C. to sym.-octahydroanthracene; and
dehydrogenating the sym.-octahydroanthracene at a chromium oxide - aluminum oxide catalyst at a temperature from about 450° C. to 550° C.

2. The method according to claim 1 wherein the hydrogenating is performed at a temperature from about 150° C. to 160° C.

3. The method according to claim 1 wherein the isomerizing is performed at a temperature of from about −10° to 0° C.

4. The method according to claim 1 wherein the dehydrogenating is performed at a temperature of from about 480° C. to 520° C.

5. The method according to claim 1 further comprising dehydrogenating the asym.-octahydrophenanthrene resulting from the separating by distillation at a chromium oxide - aluminum oxide catalyst to phenanthrene; and feeding the phenanthrene back as phenanthrene to be hydrogenated.

6. The method according to claim 1 wherein in the isomerizing of the sym.-octahydrophenanthrene from 3 to 6 weight percent aluminum chloride and from 15 to 60 weight percent methylene chloride based on the amount of sym.-octahydrophenanthrene are employed.

7. The method according to claim 6 wherein in the isomerizing of the sym.-octahydrophenanthrene from 4 to 5 weight percent aluminum chloride and from 25 to 50 weight percent methylene chloride based on the amount of sym.-octahydrophenanthrene are employed.

8. The method according to claim 1 further comprising recrystallizing the product of the dehydrogenation from a solvent to obtain pure anthracene.

9. The method according to claim 8 further comprising feeding back the mother liquor resulting from the recrystallizing after removal of the solvent as a starting material in the hydrogenating.

10. A method for hydrogenation of phenanthrene to sym.-octahydrophenanthrene comprising contacting phenanthrene with hydrogen at a pressure from about 10 to 40 bar, at a temperature from about 140° C. to 170° C. in the presence of a nickel catalyst for a time sufficient to effect hydrogenation.

11. The method according to claim 10 wherein the nickel catalyst comprises nickel deposited on a carrier.

12. The method according to claim 9 wherein the amount of nickel catalyst is from about 0.1 to 1 weight percent.

13. The method according to claim 10 wherein the contacting is performed at a pressure from about 20 to 30 bar and at a temperature from about 150° C. to 160° C.

14. A method for isomerising sym.-octahydrophenanthrene to octahydroanthracene comprising contacting the sym.-octahydrophenanthrene with an acid catalyst in the presence of a solvent and at a temperature suitable for crystallization of sym.-octahydroanthracene for a time sufficient to effect isomerization.

15. The method according to claim 14 wherein the amount of acid catalyst employed is from about 3 to 6 weight percent.

16. The method according to claim 14 wherein the acid catalyst is aluminum chloride.

17. The method according to claim 16 wherein the amount of aluminum chloride is from about 4 to 5 weight percent based on the amount of sym.-octahydrophenanthrene employed.

18. The method according to claim 14 wherein the solvent is a halohydrocarbon having a melting point below −30° C. and a boiling point above −10° C.

19. The method according to claim 18 wherein the halohydrocarbon contains at least one chlorine atom for each carbon atom in the molecule.

20. The method according to claim 19 wherein the halohydrocarbon is methylene chloride.

21. The method according to claim 20 wherein the amount of methylene chloride employed is from about 15 to 60 weight percent based on the amount of sym.-octahydrophenanthrene employed.

22. The method according to claim 21 wherein the amount of methylene chloride employed is from about 25 to 50 weight percent based on the amount of sym.-octahydrophenanthrene employed.

23. The method according to claim 14 wherein the contacting temperature is from about −30° to +5° C.

24. The method according to claim 23 wherein the contacting temperature is from about −10° C. to 0° C.

25. A method for dehydrogenation of sym.-octahydroanthracene to anthracene comprising contacting the sym.-octahydroanthracene with a chromium oxide - aluminum oxide catalyst at a temperature of from about 450° C. to 550° C. for a time sufficient to effect dehydrogenation.

26. The method according to claim 25 wherein the contacting temperature is from about 480° C. to 520° C.

27. The method according to claim 24 wherein the contacting is performed in the presence of a carrier gas.

* * * * *